(12) United States Patent
Lundblad et al.

(10) Patent No.: US 7,566,395 B2
(45) Date of Patent: Jul. 28, 2009

(54) PURIFICATION SYSTEM

(75) Inventors: Elsa Lundblad, Uppsala (SE); Lotta Hedkvist, Uppsala (SE); Henrik Sundqvist, Uppsala (SE); Markus Galin, Uppsala (SE); Thomas Pless, Uppsala (SE); Jill Simon, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 109 days.

(21) Appl. No.: 10/582,443

(22) PCT Filed: Dec. 10, 2004

(86) PCT No.: PCT/EP2004/014074

§ 371 (c)(1),
(2), (4) Date: Jan. 29, 2007

(87) PCT Pub. No.: WO2005/058452

PCT Pub. Date: Jun. 30, 2005

(65) Prior Publication Data

US 2007/0272605 A1    Nov. 29, 2007

(30) Foreign Application Priority Data

Dec. 12, 2003    (SE) .................................. 0303398

(51) Int. Cl.
*B01D 15/08* (2006.01)
(52) U.S. Cl. .................... 210/198.2; 210/143; 210/656; 210/659
(58) Field of Classification Search ................. 210/635, 210/656, 659, 143, 198.2; 96/101; 422/70
See application file for complete search history.

(56) References Cited

U.S. PATENT DOCUMENTS

| 4,546,643 | A | 10/1985 | Bonneyrat et al. |
| 5,605,663 | A | 2/1997 | Chang |
| 6,020,203 | A | 2/2000 | Rexroad, Jr. et al. |
| 6,344,172 | B1 | 2/2002 | Afeyan et al. |
| 6,508,938 | B2 * | 1/2003 | Maiefski et al. ............. 210/659 |
| 2002/0052701 | A1 * | 5/2002 | Gorenstein ................... 702/74 |
| 2002/0160521 | A1 | 10/2002 | Ozbal et al. |
| 2003/0183565 | A1 | 10/2003 | Michel et al. |

FOREIGN PATENT DOCUMENTS

WO    WO 00/12191    9/2000

OTHER PUBLICATIONS

Snyder (Introduction to Modern Liquid Chromatography, John Wiley &Sons, 1979, pp. 112-116).*
Ascalone, V., et al., "Automated High-Performance Liquid Chromatographic and Column-Switching Technique for On-Line Clean-Up and Analysis of Diltiazem in Human Plasma". Journal of Chromatography (1987), 423, p. 239-249.
Database WPI, Week 198703 Derwent Publications Ltd., London GB; Class J04, AN 1987-018623 & JP 61277055 A (Shimadzu Seisakusho KK) Dec. 8, 1986 abstract.

* cited by examiner

*Primary Examiner*—Ernest G Therkorn
(74) *Attorney, Agent, or Firm*—Yonggang Ji

(57) ABSTRACT

The present invention relates to automated chromatography systems and software for controlling such automated systems for optimising the purification of a protein from a sample. The software is adapted to monitor the signal from a detector in the system, determine two signal parameters and to control the components of the system depending on the actual values of the two signal parameters.

5 Claims, 7 Drawing Sheets

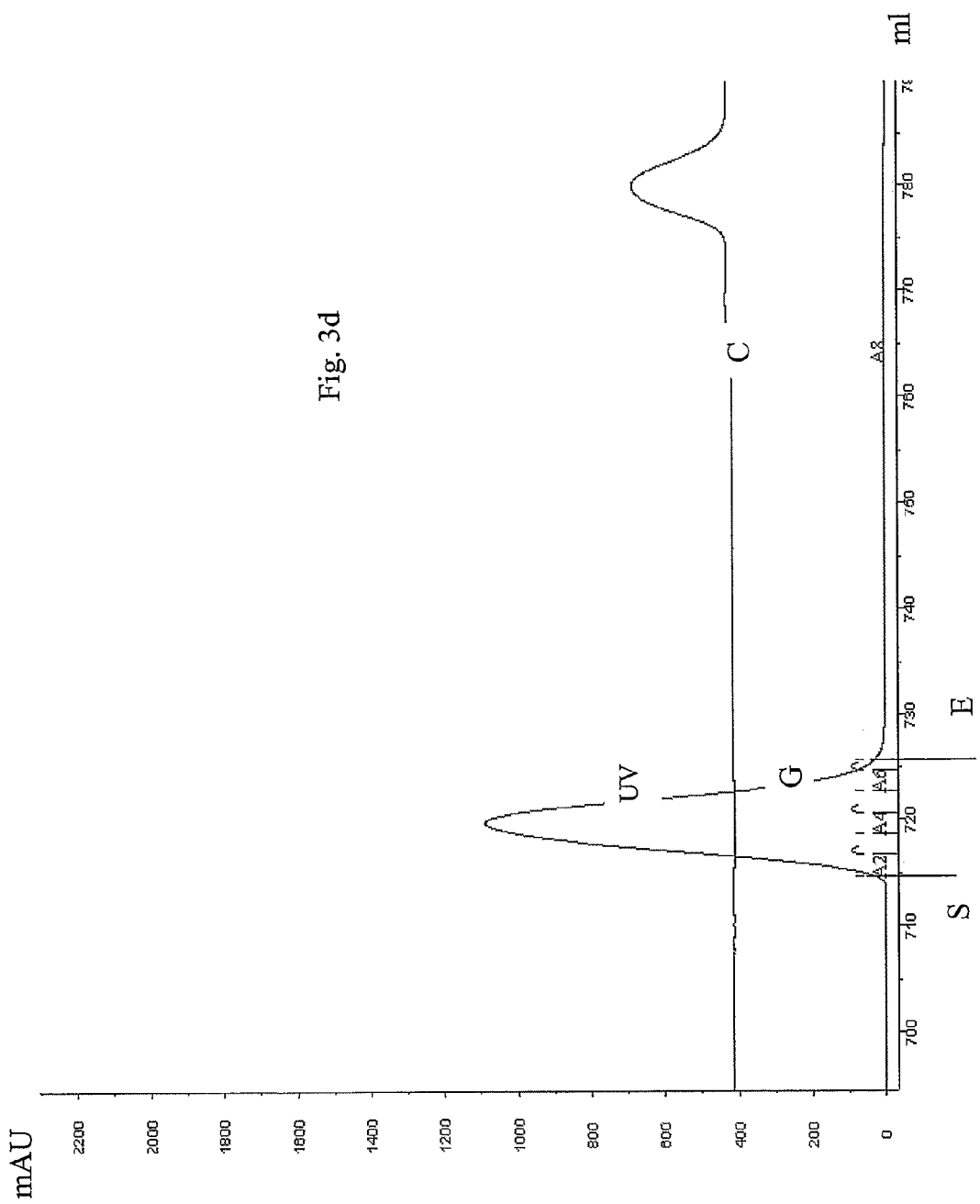

Table 1

| | Normal loading | | | | Overloading | | | |
|---|---|---|---|---|---|---|---|---|
| | Start level (mAU) | end level (mAU) | start slope (mAU/min) | end slope (mAU/min) | Start level (mAU) | end level (mAU) | start slope (mAU/min) | end slope (mAU/min) |
| GF | | | | | | | | |
| HiLoad 16/60 Superdex 75 pg | 30 | 30 | 30 | -30 | | | | |
| HiLoad 16/60 Superdex 200 pg | 30 | 30 | 30 | -30 | | | | |
| DS | | | | | | | | |
| HiPrep 26/10 Desalting | 50 | 50 | 100 | -500 | | | | |
| HiTrap Desalting | 50 | 50 | 100 | -500 | | | | |
| IEX | | | | | Only for 4-step protocols! | | | |
| RESOURCE Q, 1 ml | 30 | 30 | 20 | -50 | 100 | 100 | 100 | -100 |
| RESOURCE Q, 6 ml | 60 | 60 | 50 | -100 | 200 | 200 | 100 | -100 |
| RESOURCE S, 1 ml | 30 | 30 | 20 | -50 | 100 | 100 | 100 | -100 |
| RESOURCE S, 6 ml | 60 | 60 | 50 | -100 | 200 | 200 | 100 | -100 |
| HiTrap Q HP, 1 ml | 30 | 30 | 20 | -50 | 100 | 100 | 100 | -100 |
| 2*HiTrap Q HP, 2*1 ml | 30 | 30 | 20 | -50 | 100 | 100 | 100 | -100 |
| HiTrap SP HP, 1 ml | 30 | 30 | 20 | -50 | 100 | 100 | 100 | -100 |
| 2*HiTrap SP HP, 1 ml | 30 | 30 | 20 | -50 | 100 | 100 | 100 | -100 |
| Mono Q 5/50 GL, 1 ml | 30 | 30 | 20 | -50 | 100 | 100 | 100 | -100 |
| Mono S 5/50 GL, 1 ml | 30 | 30 | 20 | -50 | 100 | 100 | 100 | -100 |
| AC | | | | | | | | |
| HiTrap Chelating HP, 1 ml | 50 | 50 | 200 | - | 200 | 200 | 200 | - |
| HiTrap Chelating HP, 5 ml | 100 | 100 | 300 | - | 500 | 500 | 500 | - |
| HisTrap HP, 1 ml | 50 | 50 | 200 | - | 200 | 200 | 200 | - |
| HisTrap HP, 5 ml | 100 | 100 | 300 | - | 500 | 500 | 500 | - |
| GSTrap FF, 1 ml | 50 | 100 | 100 | - | - | - | - | - |
| GSTrap FF, 5 ml | 50 | 200 | 200 | - | 200 | 300 | 100 | - |
| GSTrap HP, 1 ml | 50 | 50 | 200 | - | 200 | 200 | 200 | - |
| GSTrap HP, 5 ml | 100 | 100 | 300 | - | 500 | 500 | 500 | - |

HiLoad, Sephadex, HiPrep, HiTrap, RESOURCE, Mono Q, Mono S, HisTrap and GSTrap are Trademarks of Amersham Biosciences AB

PURIFICATION SYSTEM

CROSS REFERENCE TO RELATED APPLICATIONS

This application is a filing under 35 U.S.C. § 371 and claims priority to international patent application number PCT/EP2004/014074 filed Dec. 10, 2004, published on Jun. 30, 2005, as WO 2005/058452, which claims priority to application number 0303398-2 filed in Sweden on Dec. 12, 2003; the disclosures of which are incorporated herein by reference in their entireties.

FIELD OF THE INVENTION

The present invention relates to chromatography methods, systems and software for the purification of biomolecules.

BACKGROUND OF THE INVENTION

Chromatographic separation systems are often used to separate a protein of interest from a solution containing the protein of interest and one or more contaminants. Typically, a chromatographic protein purification system comprises a plurality of chromatography columns, each having different properties, through which the solution is passed in a particular order. For example, a protein purification system may use some or all of the following 4 types of columns in turn:

affinity columns, desalting columns, ion exchange columns and gel filtration columns. Such systems can be controlled by a computer or micro processor provided with suitable software.

In order to purify a sample containing the protein of interest an operator would choose an affinity column containing a medium provided with a ligand to which the protein of interest specifically, but reversibly, binds. The sample containing the protein of interest is applied to the column under conditions that favour binding of the protein of interest to the ligand. Once the whole of the sample containing the protein of interest has been passed through the medium, the column is washed of unbound material and then the protein of interest is eluted from the medium by changing the buffer passing through the column to a buffer, for example a buffer with a high salt concentration, which breaks the bond between the protein of interest and the ligand. The presence of the protein of interest in the buffer eluted from the column is detected by a detector such as a UV-detector which detects changes in the UV absorbance at a specific wavelength, e.g. 280 nm or 254 nm, in the elution buffer leaving the column, which absorbance provides a rough measurement of total protein eluting in a given fraction. When eluting a column the fluid is collected in a fraction collector. The software monitors the UV-detector output which indicates when proteins including the protein of interest are leaving the column and records in memory to which fraction this corresponds. After the run through the first column is completed the operator checks the UV curve and manually collects the fractions of interest containing the protein. The manually collected fractions are manually pooled and transferred to the next column. If a high salt concentration elution buffer was used, then the elution buffer containing the protein of interest can be desalted by passing it through a desalting column. The elution solution outputted from the desalting column is monitored by a detector, for example, a UV-detector and the volume of desalted solution containing the protein of interest leaving the desalting column is directed to a fraction collector. The operator manually pool fractions of interest and transfer the pooled fractions to the next column. This volume of desalted solution may still contain contaminants and it may be necessary to use an ion-exchange column to remove some of them. If so, then the operator passes the volume of desalted solution containing the protein of interest through an ion exchange chromatography column which contains a medium which allows binding of the protein of interest to it. Once the volume of desalted sample containing the protein of interest has been applied to the column and the protein of interest reversibly bound to the column medium, the column can be washed to remove unbound substances. The bound substances, which include the protein of interest and possibly some contaminants, can then be removed from the medium by changing to elution conditions which are unfavourable for the ionic bonding of the protein of interest. The elution solution exiting the ion-exchange column is monitored by a detector, for example, a UV-detector and the volume of elution solution containing the protein of interest leaving the ion exchange column is collected in a fraction collector. This volume of ion-exchanged solution may still contain contaminants, e.g. aggregates of protein molecules, and it may be necessary to use a gel filtration column to remove some of them. If so, then the operator passes the volume of ion-exchanged solution containing the protein of interest through a gel filtration column. The filtered solution leaving the gel filtration is collected in a fraction collector. If the choices of medium and elution conditions in each column have been correctly chosen to favour separation of the protein of interest from the solution, then by now the protein of interest should be the substance having the highest concentration in the volume of ion-exchanged solution passing through the gel filtration column.

The above method of purifying a protein is time-consuming and laborious. It requires frequent operator actions such as evaluating the result from each column and moving fractions of elution solution from column to column.

In order to reduce these problems automated systems have been produced in which a detector signal is monitored by a computer and the collection of a fraction is started when the detector signal rises above a certain value (which corresponds to the concentration of proteins in the solution passing the detector rising above a threshold) and the collection of the fraction is stopped when the detector signal drops below a certain value (which corresponds to the concentration of proteins in the solution passing the detector falling below a threshold). In order to achieve this, the software is provided with monitoring subroutines called "Watch functions" for initiating certain actions when the absorbance detected by the UV detector passes a threshold set by the operator. A "Level Greater Than X1" watch function causes the computer to divert the flow passing the UV detector to a new container in the fraction collector and to note the number of the fraction collector that the fluid is being diverted to when the signal for the detector parameter corresponding to the absorbance level detected by the UV detector passes the value X1. It also starts a "Level Less Than Y1" watch function. A "Level Less Than Y1" watch function causes the computer to divert the flow passing the UV detector from the current container in the fraction collector to a new container (or to waste) and restarts a "Level Greater Than X1" watch function when the absorbance detected by the UV detector falls below the level Y1. While these automated systems overcome some of the problems caused by operator error, the rules which the computer follows in order to start and stop the collection of fractions have hitherto been unsophisticated. For example, the rule of starting collection when a detector signal rises above a first threshold and stopping collection when it falls below a second threshold has not been robust enough to ensure a proper collection of all the different peak shapes that have to be recognised by the software. FIG. 1 shows some examples of UV-absorbance curves which proteins can produce when leaving a column. FIG. 1 shows at A a curve with single peak which could represent a single protein leaving the column. FIG. 1 shows at B a composite curve formed of two overlapping peaks with a trough or valley between the peaks which could present two similar proteins leaving the column. Here the detector level at the lowest point of the valley is greater than half the maximum value of the first peak. It may be desired to collect these two peaks as one fraction. FIG. 1 shows at C, another composite curve formed of two overlapping peaks with a deeper valley between the peaks with a value less than half of the maximum value of the first peak which could represent two less similar proteins leaving the column. It is often desirable to collect these two peaks as separate fractions. FIG. 1 shows at D another composite curve formed of two peaks which could represent two similar proteins where the first protein is less abundant than the second protein. FIG. 1 shows at E a peak followed by a stable plateau. It is often desirable to collect the peak and plateau as separate fractions. Prior art systems which use "Level Greater Than X1" and "Level less Than Y1" can have problems separating the peaks shown in FIG. 1 at B-E.

Additionally, UV detector noise and instabilities such as instrument drift over time can lead to spurious output signals which can activate a "Level Greater Than X1" function inadvertently.

This lack of robustness means that manual intervention is still required during the separation of proteins of interest from contaminants.

SUMMARY OF THE INVENTION

According to the present invention, at least some of the problems with the prior art are solved by means of a chromatography system having the features present in the characterising part of claim 1. Software for performing a method in accordance with the present invention has the features mentioned in claim 5.

BRIEF DESCRIPTION OF THE FIGURES

FIG. 3a through FIG. 3d shows the results of elution of a sample containing proteins using a method in accordance with the present invention; and, Table 1 shows default parameter values for a range of chromatography columns.

DETAILED DESCRIPTION OF THE INVENTION

Figure 2:
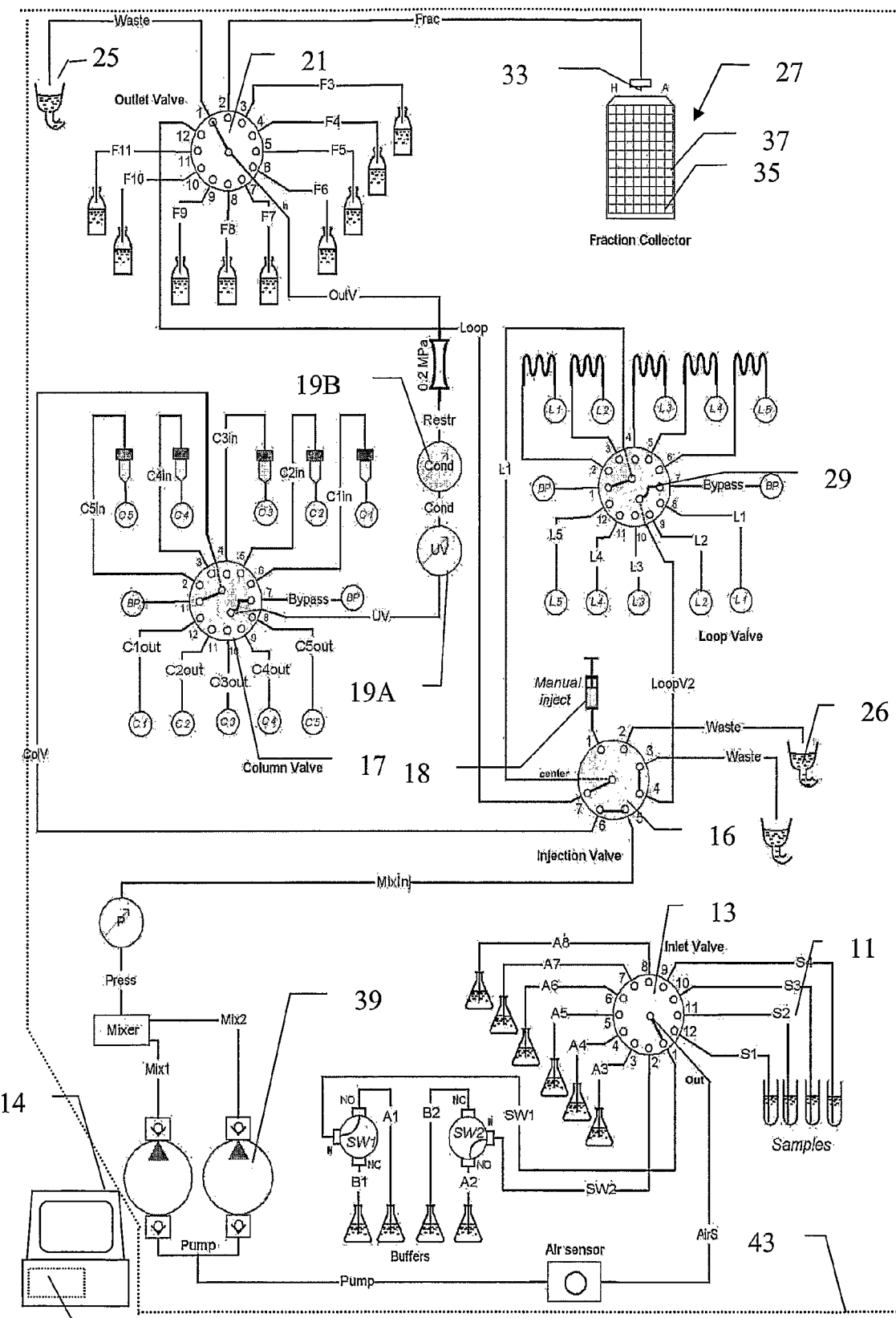
FIG. 2 shows schematically a first embodiment of a chromatography device in accordance with the present invention.
Figure 3A:
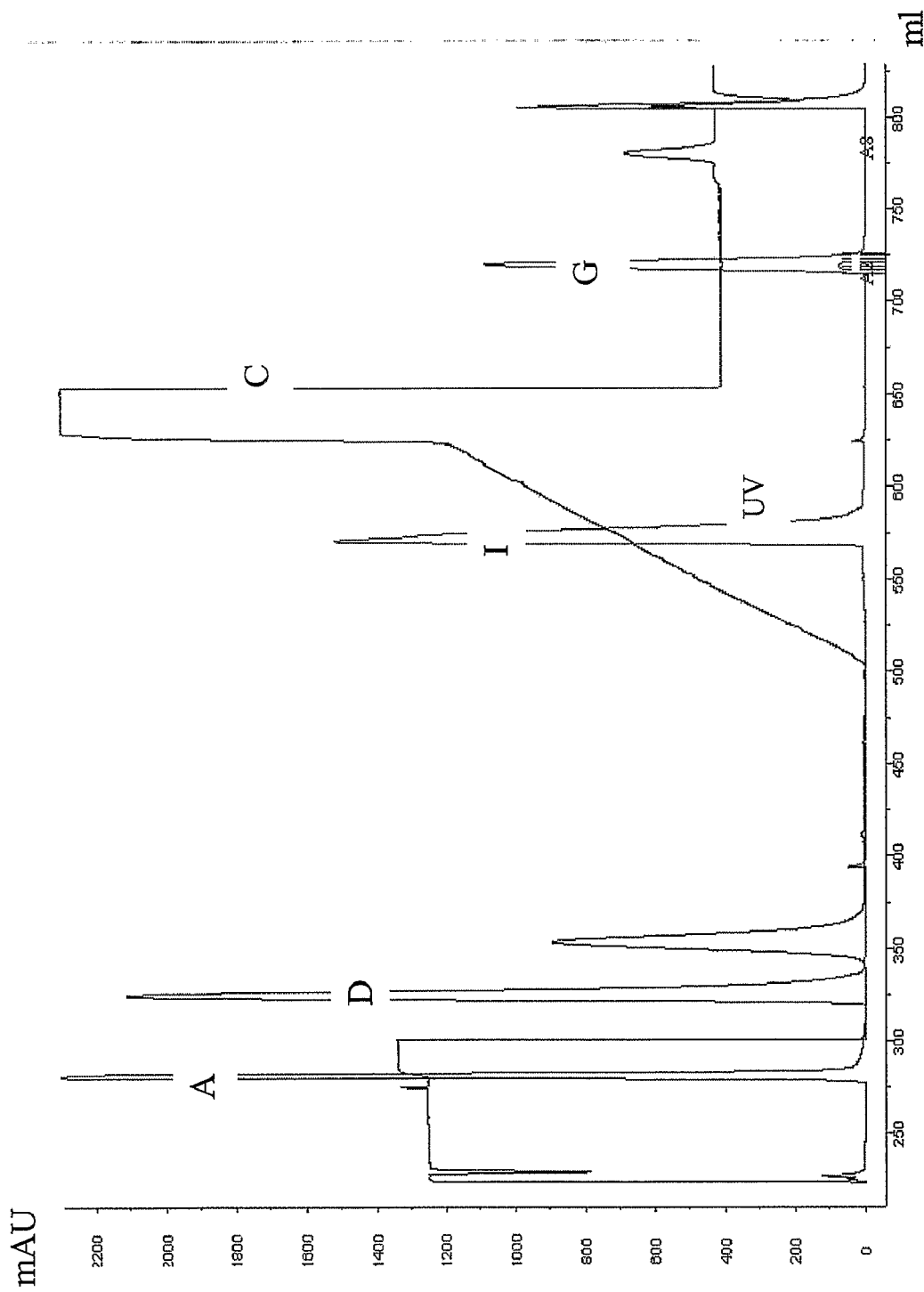
Figure 3B:
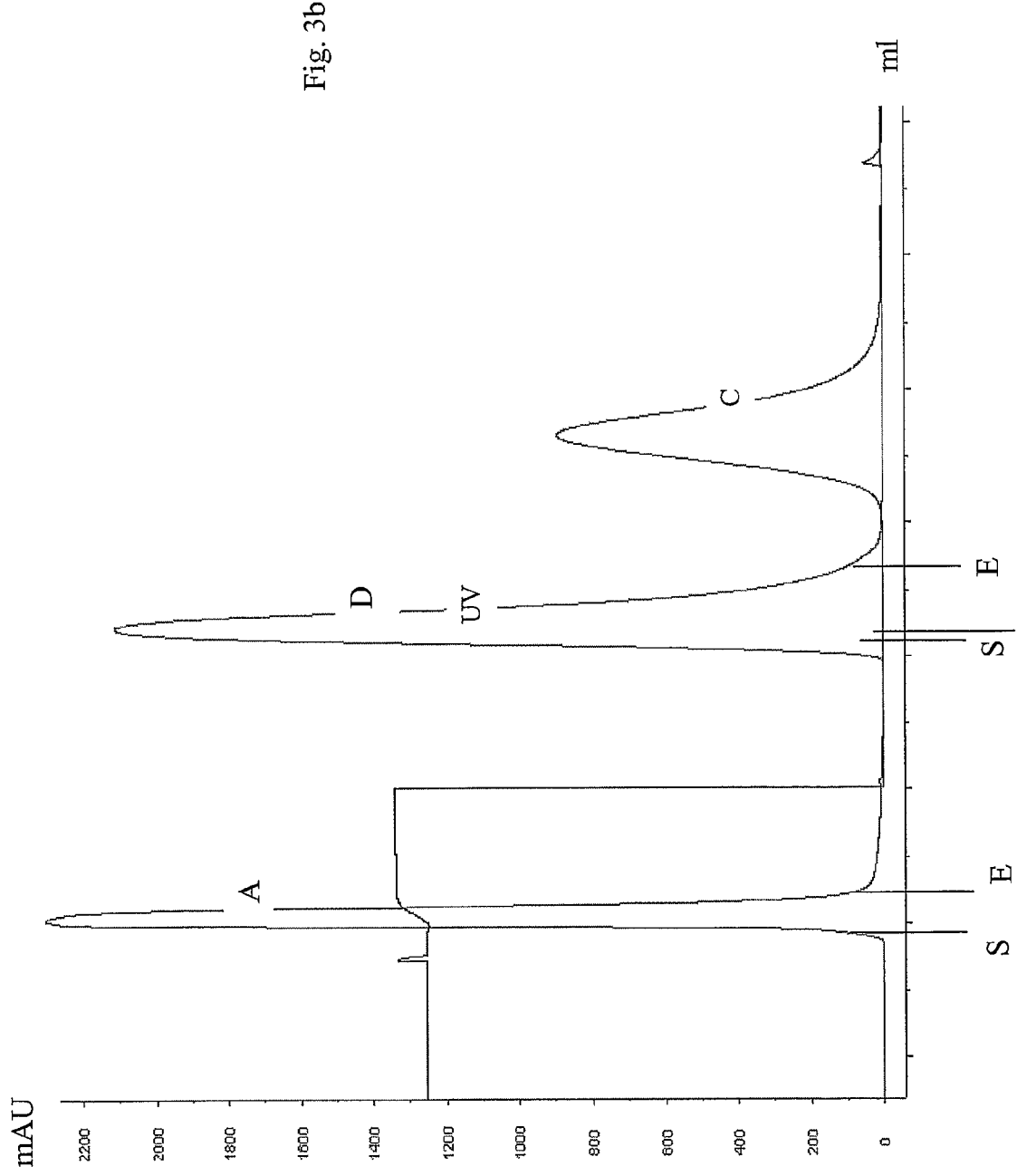
Figure 3C:
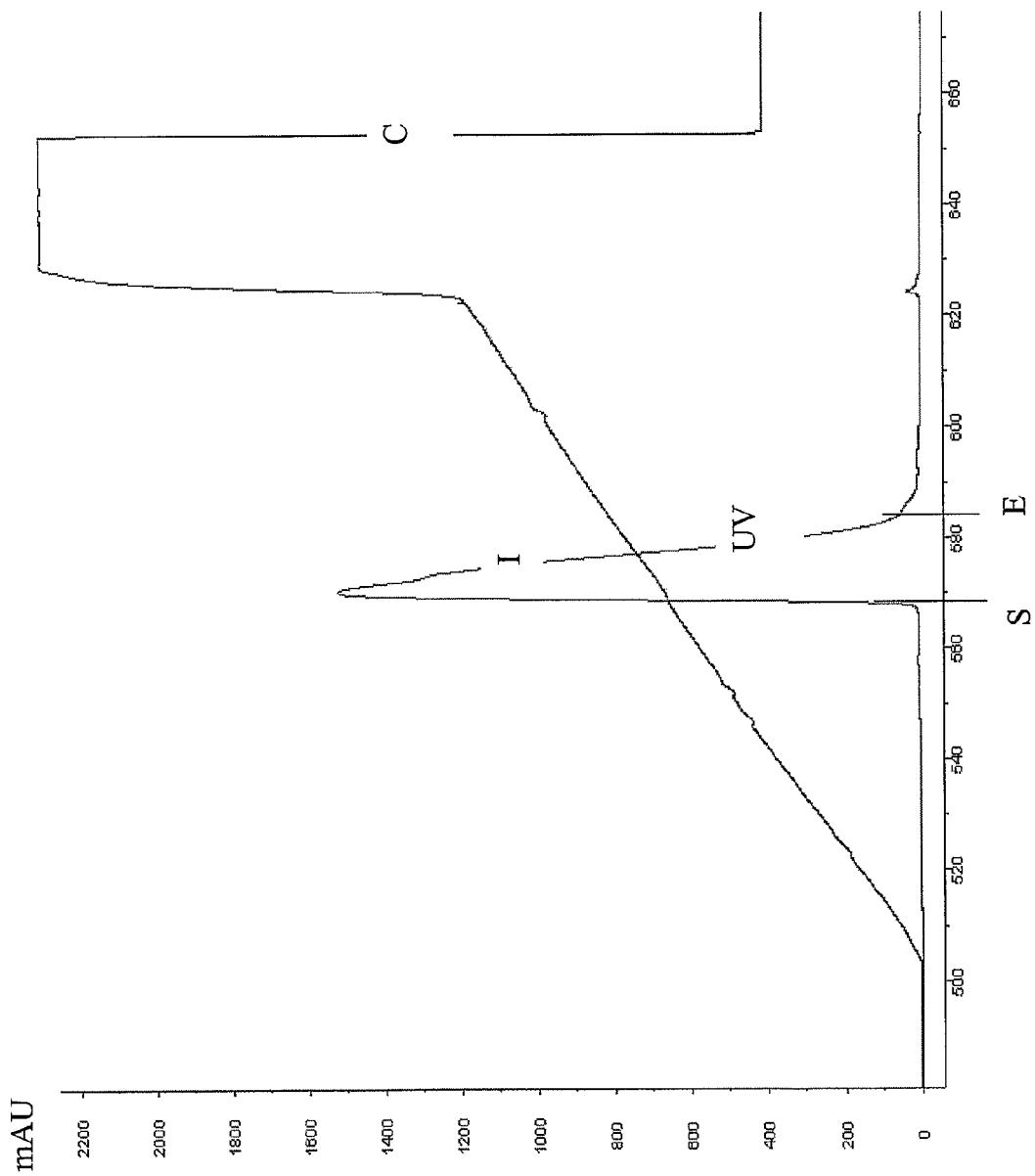

FIG. 2 shows schematically a first embodiment of an automated chromatography system 1 in accordance with the present invention for the purification a protein of interest. System 1 comprises a plurality of chromatography columns. In this embodiment of the present invention there are 5 columns C1-C5, each of which contains a different type of separation medium. Each column has an inlet end and an outlet end. In this embodiment of the present invention, columns C1 and C2, are affinity columns each of which contains a medium provided with a ligand to which a protein of interest specifically, but reversibly, binds. Column C3 is a desalting column containing a medium suitable for desalting a buffer solution containing the protein of interest. Column C4 is an ion exchange column containing a medium which allows reversible binding of the protein of interest to it. Column C5 is a gel filtration column suitable for separating the protein of interest from other proteins having different sized molecules.

Sample reservoir S1-S4, each able to contain a volume Vstart of sample liquid in which the protein of interest is in solution, are connectable to computer-controlled multipath inlet valve 13. Further reservoirs A1-A8, B1 and B2, each containing a buffer or elution solution, are also connectable to inlet valve 13. Inlet valve 13 is controllable by computer 14 to selectively direct the flow from any of the reservoirs S1-S4, A1-A8 and B1-B2 to any of the inlet ends of the columns C1-C5 via a mixer M, a computer-controlled multipath injection valve 16 and a further computer-controlled multipath column valve 17. As well as being connectable to column valve 17, injection valve 16 is connectable to a manually operable injection means 18 for the manual injection of fluid and a loop valve 29. The outlet ends of columns C1-C5 are also connectable to the computer-controlled multipath column valve 17. The outlet from column valve 17 is connectable to the fluid inlet of a detector such as a UV-detector 19A and/or conductivity detector 19B so that the liquid leaving a column C1-C5 passes through the detector. UV-detector 19A generates an output electrical signal, the strength of which varies depending on the amount of UV light absorbed by liquid passing through it and this signal is transmitted to computer 16. Conductivity detector 19B generates an output electrical signal, the strength of which varies depending on the conductivity of the liquid passing through it and this signal is transmitted to computer 16. Fluid leaving the detector(s) flows to computer-controlled multipath outlet valve 21. Outlet valve 21 is connectable to injection valve 16, a waste reservoir 25, a fraction collector 27, a plurality of fraction storage reservoirs F3-FN, and via a computer-controlled multipath loop valve 29 to the inlet ends of a plurality of storage loops L1-L5. Outlet valve 21 is controllable by computer 16 to selectively direct the liquid leaving the detector to one of injection valve 16, fraction storage reservoir F1-FN waste reservoir 25, and fraction collector 27. Loop valve 29 is computer-controllable to direct the liquid entering it to one of a plurality of loops L1-L5 or to waste reservoir 26 or back to injection valve 16. Each loop L1-L5 comprises a length of tubing of such length that its internal volume is between 1% and 100% of the volume Vstart of the sample. The outlet ends of loops L1-L5 are each connectable to a separate inlet of the loop valve 29. Loop valve 29 has an outlet connectable via injection valve 16 to column valve 17 and is controllable to connect the outlet end of any of loops L1-L5 to column valve 17. The fraction collector 27 is movable and comprises a fixed outlet pipe 33. Under the control of the computer 16 fraction collector 27 can be moved so that 33 is positioned above fraction collecting reservoirs, e.g. wells 35 in a micro-titre plate 37. In order to cause the liquids in the system to flow, the system comprises pump 39, the pumping rate and direction of which is under the control of computer 14. Preferably the pump, valves, columns, loops, detector and fraction collector are all mounted together in or on a housing 43 (shown by a dashed line) to form a single unit. Such a unit is available from Amersham Biosciences AB, Uppsala, Sweden under the name ÄktaXpress™.

The computer 14 is provided with memory 45 containing software for controlling the operation of the pump, valves and fraction collector and for processing the out signal from the detectors) 19A, 19B. A suitable software program is available from Amersham Biosciences Ab, Uppsala, Sweden and is called Unicorn™ version 5.00.

By appropriate control of the valves and pumps, the above-described arrangement is able to move precise volume of liquids from sample reservoir 11 to any other part of the system. For example, let us assume that the sample is a partly purified protein solution comprising a mixture of proteins in which the protein of interest is the largest component and the remaining components are unwanted. Let us also assume that the operator knows that the protein of interest can be separated from the contaminants by passing the sample solution in order through appropriate affinity, desalting, ion exchange and gel filtration columns. Before starting the purification, the operator of the system would connect the appropriate chromatography columns C1-C5 to the unit 43 and put the sample containing the protein of interest into sample reservoir 11. The operator would then program the software to perform the purification by selecting the order that the sample solution is to be fed to the chromatography columns C1-C5 and either setting detector signal thresholds which cause the program to perform certain actions or choosing the default detector signal threshold settings set by the manufacturer. The software is able to perform the following functions:

select which peak is to be transferred to the next column;
reinject a selected peak to the next column;
collect a pair of overlapping peaks in two separate fractions if the detector signal satisfies certain conditions; and
separate a peak followed by a plateau into a fraction containing the peak and a second fraction containing the plateau if the detector signal satisfies certain conditions.

The software first commands valve 13 to connect sample reservoir 11 to the inlet of column C1 via injector valve 16 so that 39 can suck the sample solution containing the protein of interest from the sample reservoir 11 to and through the affinity column C1. The protein of interest and other similar containment proteins bind to the ligands on the medium in column C1 while other contaminants pass though column C1. These contaminants can be sent via outlet valve 21 to one of the reservoirs F3-FN. Once the sample solution has been loaded onto affinity column C1 the software causes unbound contaminants to be washed out of the column by passing a wash solution from one of the reservoirs A1-A8, B1-B2 through the column. The wash solution can also be sent to one of the reservoirs F3-FN as a safety precaution so that no material is lost. In order to release the bound proteins from the affinity medium it is necessary to elute the column C1 with an elution buffer gradient, for example a buffer solution which contains a predefined concentration of a second component, e.g. salt, through the column, from another of the reservoirs A1-A8, B1-B2. This elution buffer is able to break the bonds binding the protein of interest to the affinity chromatography medium and the protein of interest is carried in the elution buffer out of the column C1 . The outputted elution buffer passes UV-detector 19A arranged to measure the strength of a beam of UV-light after it has passed through the elution buffer. The UV-detector 19A produces a detection signal which varies in dependence on the amount of UV-light absorbing material in the elution buffer and this signal is transmitted to computer 14. The software watches the detection signal and processes it in order to identify two signal parameters: the current signal level and the current rate of change ("slope") of the signal level. Once the signal passes a "Greater than" threshold signal strength indicating the presence of proteins in the eluted liquid, the software controls valve 21 to direct the eluted fluid from the column to a first loop L1-L5. At the same time a timer may be started. As the flow rate from the pump in ml/min is controllable by the computer 14 and therefore is known, it is possible for the computer 14 to calculate the volume of liquid flowing into the first loop L1. As the volume of the loop L1 is known, it is possible for the computer 14 to arrange for the liquid containing the protein of interest to be switched from the first loop L1 to a second loop, e.g. L2, if the volume of liquid containing the protein of interest has a greater volume that the volume of the first loop L1. Once the signal falls below a "Lower than" threshold signal strength indicating the absence of protein in the eluted fluid, the computer 14 causes valve 29 to direct the eluted liquid from the column C1 to the waste reservoir 26. It stores in the memory 45 which loop it has put the eluted buffer in and the volume of eluted buffer stored in the loop. If the signal strength again passes the "Greater than" threshold signal strength, the software controls valve 29 to direct the eluted liquid from the column to a further loop e.g. L3 where the eluted liquid is collected. This continues until the signal strength once again falls below "Lower than" threshold signal strength indicating the absence of protein in the eluted fluid, at which time the computer causes valve 29 to direct the eluted liquid from the column C1 to the waste reservoir 26. During collection of eluted liquid in a loop the software records the highest absorbance value and/or performs an integration of the absorbance signal. The integral of the absorbance signal gives a measure of the total amount of protein collected in that loop. The computer continues to pump elution buffer through the column C1 until a predetermined volume of elution buffer has been passed through the affinity column C1. At this stage, at least one of the loops L1-L5 contains a volume of eluted buffer containing the protein of interest. The software checks the memory and determines which of the loops L1-L5 contains the largest integral of the absorbance signal or, alternatively, the highest absorbance value of eluted buffer. The choice of whether to check for the largest integral of the absorbance signal or the highest absorbance value can be pre-programmed by the software producer or can be made user selectable or could be made on the basis of the values recorded by the software. For example if there are two loops with substantially the same integral of the absorbance signal then the software could check which of the two loops have the highest absorbance value and choose this loop. This loop, e.g. loop L1 is assumed to contain the protein of interest (as the affinity medium was chosen to bind the protein of interest) and the software operates valves 13, 17, 21 and 29 to direct the volume of eluted buffer in loop L1 to the desalting column C3. The buffer in any of the other loops which also contains proteins may also be saved in one of the reservoirs in case it turns out that the protein of interest was not in the loop containing the largest integral of the absorbance signal or, alternatively, the highest absorbance value of eluted buffer but it was in another loop. The desalted buffer assumed to be containing the protein of interest is outputted from column C3 to the UV detector 19A. The signal strength from the UV detector is used by the software as described above to determine when peaks of proteins in the desalted buffer pass the UV detector and to feed the volumes of desalted buffer into one or more loops. Once all the selected volume of eluted buffer has been the desalted, the software determines which of the loops contains the largest integral of the absorbance signal or, alternatively, the highest absorbance value of desalted buffer and assumes that this loop contains the protein of interest. The volume of desalted buffer in this loop, e.g. L3 is then fed to the ion-exchange column C4. The buffer in any of the other loops which also contains proteins may also be saved in one of the reservoirs in case it turns out that the protein of interest was not in the loop containing the largest integral of the absorbance signal or, alternatively, the highest absorbance value of eluted buffer but it was in another loop. The ion-exchanged buffer containing the protein of interest is outputted from ion exchange column C4 to the UV detector 19A. The signal strength from the UV detector 19A is used by the software as described above to determine when peaks of proteins in the ion-exchanged buffer pass the UV detector 19A and to feed the volumes of ion-exchanged buffer into one or more loops L1-L2, L4-L5. Once all the volume of desalted buffer from the loop has been ion-exchanged, the software determines which of the loops contains the largest integral of the absorbance signal or, alternatively, the highest absorbance value of ion-exchanged buffer and assumes that this loop, e.g. L4 contains the protein of interest. The volume of ion-exchanged buffer in this loop, e.g. L4 is then fed to the gel-filtration column C5. The buffer in any of the other loops which also contains proteins may also be saved in one of the reservoirs in case it turns out that the protein of interest was not in the loop containing the largest integral of the absorbance signal or, alternatively, the highest absorbance value of eluted buffer but it was in another loop. The filtrated buffer containing the protein of interest is outputted from gel filtration column C5 to the UV detector 19A. The signal strength from the UV detector 19A is used by the software as described above to determine when peaks of proteins in the filtrated buffer pass the UV detector 19A and to feed the volume of gel-filtrated buffer to the fraction collector 27 and collect the peaks in one or more wells 35. It can then be tested to ensure that the correct protein has been purified. The software tracks where all the peaks from the columns are stored. This is useful if the wrong protein has been collected as the purification can be rerun using the fluid containing peaks saved from the other loops.

In addition to The "Level Greater than X1" and "Level less than Y1" watch functions, devices and methods in accordance with a first embodiment of the present invention are provided with "Slope Greater Than X2" and "Slope Less Than Y2" watch functions. A "Slope Greater Than X2" watch function causes the software to divert the fluid leaving the UV detector to a new fraction collector container when the absorbance level detected by the UV detector increases at a rate greater than X2 mAU/min. The rate of change parameter can be called the "slope" of the signal. Similarly, a "Slope Less Than Y2" causes the software to divert the fluid leaving the UV detector to a new fraction collector container when the absorbance level detected by the UV detector decreases at a rate less than Y2 mAU/min. The software is arranged to be able to watch two watch functions at the same time e.g. "Level Greater Than X1" and "Slope greater Than X2" and to only take action if the conditions to activate both functions are present, i.e. the level is greater than X1 and the slope is greater than X2.

In addition to the previously mentioned watch functions, devices and methods in accordance with a further embodiment of the present invention are also provided with "Peak Maximum with Factor Z1" where Z1 is a factor which is less than 1 of the maximum peak height. For example if the maximum absorbance level of a peak is detected to be 2000 mAU and Z1 is set at 0.5, then the watch function "Peak Maximum with Factor 0.5" will cause an action when the detector level fall below 1000 mAU. This action could be to stop storing the fluid in a loop and/or to note that a peak has ended and/or to start a different watch function.

Figure 1:
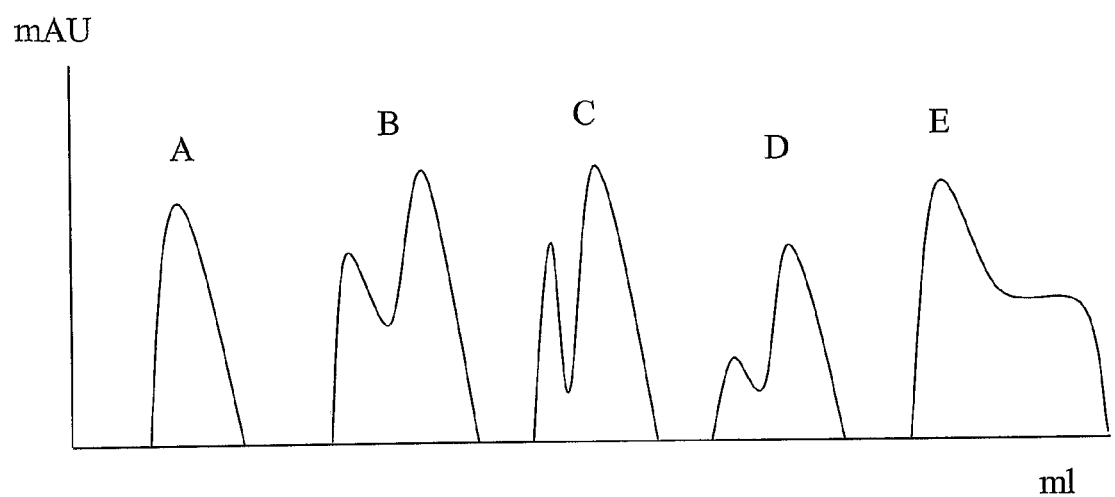
FIG. 1 shows examples of possible detector signal peak shapes for proteins leaving a chromatography.

In addition to the previously mentioned watch functions, devices and methods in accordance with another embodiment of the present invention are also provided with "Valley" and "Stable Plateau" watch functions. A valley is formed between two overlapping peaks—see for example Fig B and C. This may be defined in the software as occurring when the detector signal is greater than a certain level e.g. X1 and a local minimum occurs i.e. the slope of the detected signals changes from falling signal to a rising signal. A stable plateau is shown in FIG. 1 at E. In the software this is defined as occurring when the detector signal remains at a constant value (with a certain allowable variation) for a predetermined period of time. The software can be adapted to look for three or more watch functions at the same time. For example, in order to save two closely overlapping peaks as shown in FIG. 1 at B in one fraction but to save two less closely overlapping peaks as shown in FIG. 1 at C into two fractions, the software could be arranged to look for "Level Greater Than X1" and "Slope greater than X2". Once the level values and slope are above X1 resp. X2, then the software could record the start of a peak, switch the fluid to a loop, start a timer to measure the filling of the loop and start the watch function "Peak max with factor 0.5". This causes the computer to record the maximum detector level signal and to take a further action when the signal level drops to 0.5 times its maximum level. This further action could be to look for "Level less than Y1 or Valley or Stable Plateau". If the lowest value of the valley between the peaks is above 0.5 times the maximum value of the first peak as shown in FIG. 1 at B then the conditions for causing an action under "Peak Maximum with Factor 0.5" will only occur after both peaks have been collected as one fraction. If the lowest value of the valley fall below 0.5 times the maximum value of the first peak then three different events may subsequently occur:

a) the signal level may continue to fall until it passes the less than threshold Y1—this would correspond to a simple peak as shown in FIG. 1 at A. The software would then stop collecting the fluid in the current loop, send the following fluid to waste and reset the "Level greater Than X1" and "Slope greater Than X2" watch commands;

b) the signal level may start to rise again corresponding to overlapping peaks as shown in FIG. 1 at C. The software would then stop collecting the fluid in the current loop, send the following fluid to a new loop and reset the "Level greater Than X1" and "Slope greater Than X2" watch commands;

c) the signal may remain constant indicating a plateau as shown in FIG. 1 at E. The software would then stop collecting the fluid in the current loop, send the following fluid to different and active a ("Level greater Than X1" and "Slope greater Than X2") or ("Level less than Y1" and "Slope less Than Y2") watch.

In addition to the previously mentioned watch functions, devices and methods in accordance with yet another embodiment of the present invention may also be provided with one or more of the following watch functions:

("Level Greater Than X1" or Slope Greater Than Y1") which would cause the software to take action if the detector signal fulfils one of the level or slope conditions;

("Slope Less Than Y2" and "Peak Maximum with Factor Z1") which would cause the software to take action if the detector signal rate of change falls below Y2 monitor units/minute (e.g. mAU/min) and the level falls to the specified fraction "Factor Z1" of the most recent peak maximum;

(Level Less Than X2" and (("Slope Less Than Y2" and "Peak Maximum with Factor Z1")) would cause the software to take action if the detector signal fall below the level X2 and at the same time the signal rate of change falls below Y2 monitor units/minute and the level falls to the specified fraction "Factor Z1" of the most recent peak maximum; and (Level Less Than X2" or (("Slope Less Than Y2" and "Peak Maximum with Factor Z1")) would cause the software to take action if the detector signal fall below the level X2, or if the signal rate of change falls below Y2 monitor units/minute and the level falls to the specified fraction "Factor Z1" of the most recent peak maximum; and, ("Stable Plateau" or (("Slope Less Than Y2" and "Peak Maximum with Factor Z1")) would cause the software to take action if the detector signal stays with predetermined limits for a predetermined period of time, or if the signal rate of change falls below Y2 monitor units/minute and the level falls to the specified fraction "Factor Z1" of the most recent peak maximum.

In one embodiment of the present invention, the software is provided with a "set-up wizard". This is a program which allows an operator to input the identity of the columns being used in the system and then select either default watch function threshold values suggested by the software and shown on a user interface such as a screen or to input his own threshold values. The default values are stored in the computer memory and are values which have been inputted by the system manufacturer and/or column manufacturer. The default values are values which have been tested on the columns and which have been proven to provide satisfactory separation of the target protein of interest. Table 1 shows a list of default values for HiLoad Superdex™ gel filtration columns, HiPrep™ desalting columns, RESOURCE Q™, RESOURCE S™, HITrap Q™, HiTrap SP™ and Mono Q™ ion exchange columns and HiTrap Chelating™, HisTrap HP™, GSTrap™ affinity columns from Amersham Biosciences, Uppsala, Sweden. The provision of such default values can save a lot of operator time as it avoids the necessity of the operator to perform a series of experiments to find his own optimum threshold levels. In the case that the operator wishes to experiment with his own threshold values, then the fact that the software can display suggested default values to the user, gives the user a baseline from which to experiment from and can reduce the number of experiment needed to find the optimum threshold values.

FIGS. 3a-3d show an example of a 4-step protein purification of a E. Coli lysate sample on an ÄktaXpress™ using Unicorn™ version 5.00 software where the user has used the set-up wizard to input the column types and elected to use the default values shown in Table 1 for the level and slope watch function thresholds. The target protein was a (His)6 tagged protein. The following columns were used: Affinity: HisTrap HP 5 ml, Desalting: HiPrep 26/10 Desalting, Ion Exchange: RESOURCE Q 6 ml, Gel Filtration: HiLoad 16/60 Superdex 75 Prep Grade. The software used the following watch functions: ("Level greater Than X1" And "Slope Greater Than X2"), ("Level Less Than Y1" or "Valley" or "Stable Plateau") and the "Peak Maximum with Factor Z1" used a factor (Z1) of 0.2 for the affinity column and 0.5 for the ion exchange and desalting columns.

In FIGS. 3a-3d, the signal UV from a UV-detector and the signal C from a conductivity detector are plotted against ml of fluid passing the detectors. Peaks starts are indicated in the figures by S and peak ends by E. The sample is applied to an affinity column and the affinity peak A (shown in more detail in FIG. 3b) is first collected in a loop and later applied to a desalting column. The peak D (shown in more detail in FIG. 3b) eluting from the desalting column is collected in a loop and later applied to an ion exchange column. The peak I (shown in more detail in FIG. 3c) eluting from the ion-exchange column is collected in a loop and later applied to a gel filtration column. The peak eluting G (shown in more detail in FIG. 3d) from the gel filtration column is collected in wells A1-A7 in the fraction collector.

While the invention has been illustrated by an example of a system in which one computer running the Unicorn™ version 5.00 software is used to purify one protein on one ÄktaXpress™ unit, it is conceivable to use the same computer and Unicorn™ version 5.00 software to control a plurality of ÄktaXpress™ units simultaneously and to purify more than one protein on each ÄktaExpress™ unit.

The above mentioned embodiments are intended to illustrate the present invention and are not intended to limit the scope of protection claimed by the following claims.

The invention claimed is:

1. An automated chromatography system for the purification of a proteins, comprising a plurality of chromatography columns, a plurality of computer-controlled valves, a pump, at least one loop for the storage of fluid, a detector able to produce an output signal representing the composition of a fluid passing through the detector, a computer provided with and adapted to run software for controlling said valves, pump and detector, wherein said software is able to process the output signal of said detector to identify two signal parameters which parameters are the signal level and the rate of change of the signal level, further wherein said software is adapted to control the system to start and stop the storing of said fluid in the at least one loop when predetermined conditions for one or both of said signal parameters are fulfilled.

2. The automated chromatography system of claim 1, wherein said software is adapted to perform predetermined actions when predetermined conditions for said two signal parameters are fulfilled at the same time.

3. The automated chromatography system of claim 2, wherein said predetermined conditions for said two signal parameters are default conditions or operator selected conditions.

4. The automated chromatography system of claim 1, wherein said software is adapted to perform predetermined actions when predetermined conditions for one of said two signal parameters is fulfilled.

5. The automated chromatography system of claim 4, wherein said predetermined conditions for said two signal parameters are default conditions or operator selected conditions.

* * * * *